(12) United States Patent
Kaneko et al.

(10) Patent No.: US 11,872,550 B2
(45) Date of Patent: Jan. 16, 2024

(54) SAFETY CABINET

(71) Applicant: Hitachi Industrial Equipment Systems Co., Ltd., Tokyo (JP)

(72) Inventors: Takeshi Kaneko, Taina (JP); Takeshi Matsumura, Taina (JP)

(73) Assignee: Hitachi Industrial Equipment Systems Co., Ltd., Tokyo (JP)

( * ) Notice: Subject to any disclaimer, the term of this patent is extended or adjusted under 35 U.S.C. 154(b) by 583 days.

(21) Appl. No.: 17/256,344

(22) PCT Filed: Jun. 29, 2020

(86) PCT No.: PCT/JP2020/025566
§ 371 (c)(1),
(2) Date: Dec. 28, 2020

(87) PCT Pub. No.: WO2022/003791
PCT Pub. Date: Jan. 6, 2022

(65) Prior Publication Data
US 2022/0184597 A1    Jun. 16, 2022

(51) Int. Cl.
*B01L 1/00* (2006.01)
*C12M 1/00* (2006.01)
*A61L 2/26* (2006.01)
*F24F 7/06* (2006.01)

(52) U.S. Cl.
CPC .............. *B01L 1/00* (2013.01); *A61L 2/26* (2013.01); *C12M 1/00* (2013.01); *F24F 7/06* (2013.01); *A61L 2202/11* (2013.01); *A61L 2202/121* (2013.01)

(58) Field of Classification Search
CPC ............. C12M 41/14; B01L 1/00; B25J 21/00
See application file for complete search history.

(56) References Cited

U.S. PATENT DOCUMENTS

| 2003/0138942 | A1* | 7/2003 | Cecchi ................... C12M 41/36 435/303.1 |
| 2005/0084956 | A1* | 4/2005 | Tamaoki ................ C12M 41/14 435/303.1 |
| 2013/0052927 | A1  | 2/2013 | Broemsen et al. |
| 2018/0001315 | A1* | 1/2018 | Kaneko .................... B01L 1/02 |
| 2018/0044625 | A1* | 2/2018 | Chikuda .................. C12M 1/00 |

(Continued)

FOREIGN PATENT DOCUMENTS

| CN | 102962239 A | 3/2013 |
| JP | 2000-342243 A | 12/2000 |
| JP | 2006-122816 A | 5/2006 |

(Continued)

OTHER PUBLICATIONS

English translation of Ono JP 2006043521 (generated 2023).*

(Continued)

*Primary Examiner* — Nathan A Bowers
(74) *Attorney, Agent, or Firm* — Crowell & Moring LLP

(57) ABSTRACT

A safety cabinet includes a work space where work is performed; a front panel disposed in a front surface of the work space; and an air cleaner that cleans air to be supplied to the work space. An imaging device is disposed on one side surface side of side surfaces of the work space, and a connection opening is disposed on the other side surface side facing one side surface.

5 Claims, 8 Drawing Sheets

(56) References Cited

U.S. PATENT DOCUMENTS

2020/0121818 A1    4/2020   Kaneko

FOREIGN PATENT DOCUMENTS

| JP | 2006-43521 A | 2/2016 |
| JP | 2018-83151 A | 5/2018 |
| WO | WO 2019/207894 A1 | 10/2019 |
| WO | WO 2020/012853 A1 | 1/2020 |

OTHER PUBLICATIONS

English translation of Takayama WO 2020012853 (generated 2023).*
International Search Report (PCT/ISA/210) issued in PCT Application No. PCT/JP2020/025566 dated Jul. 21, 2020 (three (3) pages).
Japanese-language Written Opinion (PCT/ISA/237) issued in PCT Application No. PCT/JP2020/025566 dated Jul. 21, 2020 (six (6) pages).

* cited by examiner

SAFETY CABINET

TECHNICAL FIELD

The present invention relates to a safety cabinet.

BACKGROUND ART

In regenerative medicine that repairs or replaces a lost function, or in cell therapy that injects cells to treat or alleviate diseases or damage, production is required to be performed in a work space having a certain degree of cleanliness in a production environment in a treatment process before culturing using cells or tissues (hereinafter, referred to as a "sample") extracted from a patient. In addition, the production environment requires reducing the risk of contamination to the sample. Furthermore, the production environment requires preventing the sample from being diffused into a work chamber. Furthermore, the production environment requires preventing mutual contamination between different samples.

The reason is that when cells of an animal or another person are mixed with the sample, the cells are recognized as foreign matter in the body and are rejected by an immune reaction to be dropped out.

In addition, in an environment where sterile drugs, biological drugs, or the like are produced, production is performed in a work space having a certain degree of cleanliness to reduce the risk of contamination to the drugs or the like. Furthermore, in research where pathogens or the like are handled or genes are manipulated, biohazard countermeasures are taken to physically isolate the human and environment from the biological materials and the pathogens.

There is a safety cabinet as a device providing the space. In the safety cabinet, air is delivered by air blowing means, and the air passes through a HEPA filter which is an air cleaner, so that dust contained in the air is removed and then the air is supplied to a predetermined space.

Patent Document 1 discloses a safety cabinet. Patent Document 1 describes a configuration where a monitor screen that displays information required for work in the safety cabinet is provided on a back surface of a work space and information read by a barcode reader or values measured by an electronic balance are displayed on the monitor screen.

CITATION LIST

Patent Document

Patent Document 1: JP 2006-122816 A

SUMMARY OF THE INVENTION

Problems to be Solved by the Invention

For the purpose of investigating a cause and preventing recurrence when an error occurs in cell culturing, an imaging device such as a network camera is required to be attached to the safety cabinet to record work.

The inside of a work chamber of the safety cabinet is covered with an SUS304 plate to prevent corrosion, and thus has high light reflectance. For this reason, when a network camera is installed on a back surface of the work chamber, light from an illumination lamp provided in the safety cabinet directly or indirectly illuminates the network camera, so that it is difficult to watch a captured video, and the entirety of the work space in the work chamber cannot be properly monitored due to the angle of view of a lens of the imaging device, which is a problem.

Patent Document 1 describes the monitor screen that displays information required for work in the safety cabinet, but does not consider an imaging device capable of sufficiently monitoring the inside of the work space of the safety cabinet.

An object of the present invention is to provide a safety cabinet including an imaging device capable of properly monitoring a work space.

Solutions to Problems

As one exemplary example of the present invention, there is provided a safety cabinet including: a work space where work is performed; a front panel disposed in a front surface of the work space; and an air cleaner that cleans air to be supplied to the work space. An imaging device is disposed on one side surface side of side surfaces of the work space, and a connection opening is disposed on the other side surface side facing one side surface.

Effects of the Invention

According to the present invention, a safety cabinet including an imaging device capable of properly monitoring a work space can be realized.

MODE FOR CARRYING OUT THE INVENTION

Embodiments of the present invention will be described with reference to the drawings.

First Embodiment

Figure 1:
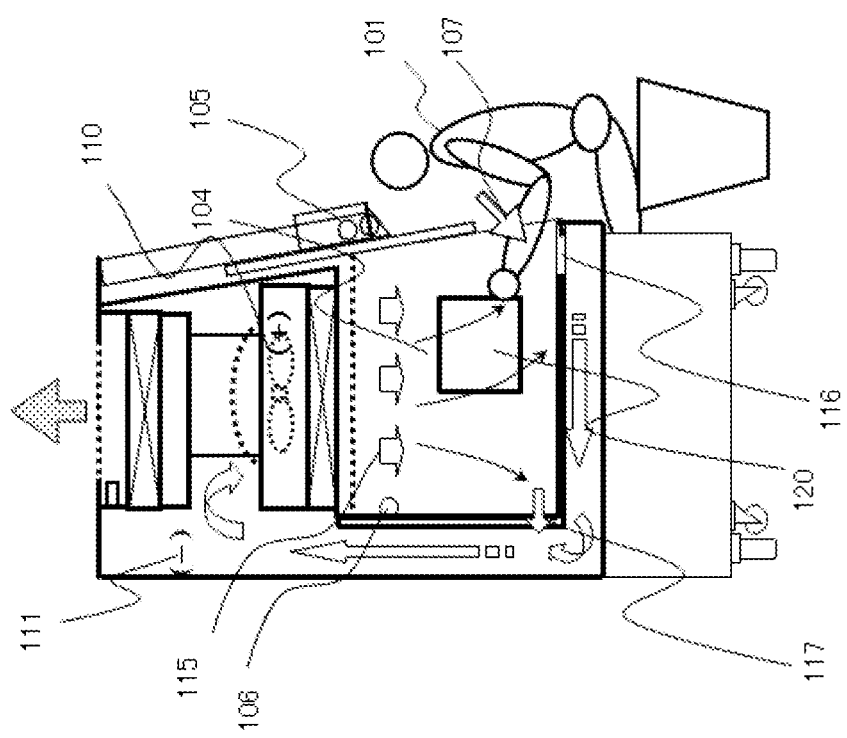
FIG. 1 is an internal structural view of a safety cabinet in a first embodiment as seen in a left side direction.
Figure 2:
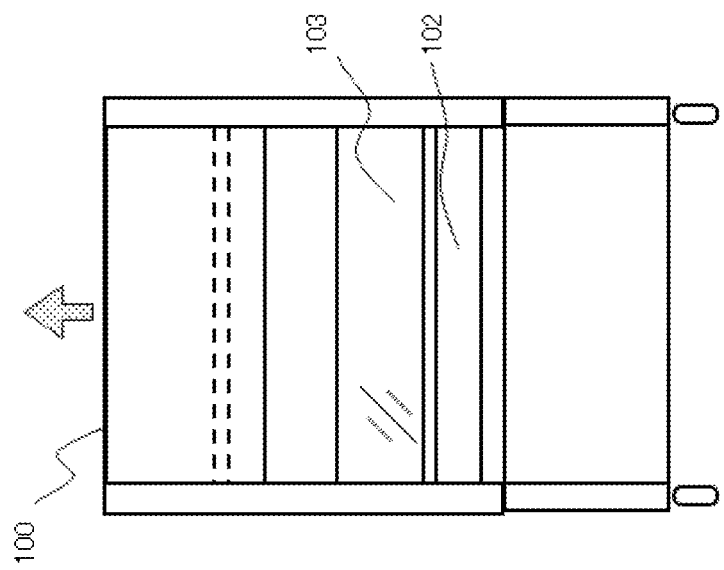
FIG. 2 is an exterior front view of the safety cabinet in the first embodiment as seen from the front.
Figure 3:
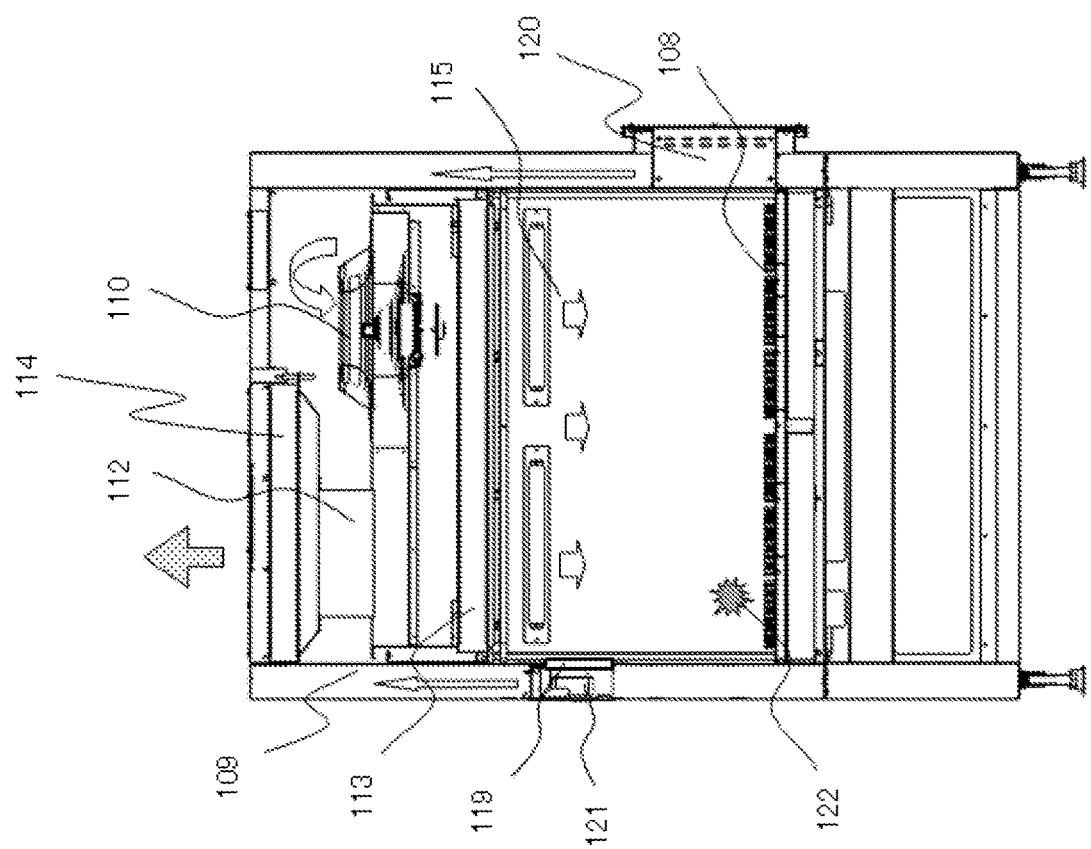
FIG. 3 is an internal structural view of the safety cabinet in the first embodiment as seen from the front.

FIGS. 1 to 3 are views illustrating a structural example of a safety cabinet 100 according to Japanese Industrial Standards (JIS) K3800 in a first embodiment.

FIG. 1 is an internal structural view of the safety cabinet 100 of the first embodiment as seen in a left side direction.

FIG. 2 is an exterior front view of the safety cabinet 100 of the first embodiment as seen from the front.

FIG. 3 is an internal structural view of the safety cabinet 100 of the first embodiment as seen from the front.

A worker 101 inserts the arms into a work space 104 from a front opening 102 of the safety cabinet 100 to perform work while seeing the inside of the work space 104 from a front shutter 103. The illuminance suitable for work is maintained in the work space 104 by an illumination lamp 105. In addition, a sterilization lamp 106 is generally provided in an upper portion of a back surface of the work space 104. The sterilization lamp 106 is used as an auxiliary unit to sterilize the inside of the work space 104 before and after work, together with decontamination by wiping with 70% alcohol or the like.

Air 107 in a general chamber which is suctioned from the front opening 102 is suctioned into a blower 110 through a circulation flow path 109 including a lower portion of a work bench 108 (lower surface of the work space 104), a side surface and the back surface of the work space 104, and a main body portion of the safety cabinet 100. A region up to a suction side of the blower 110 through which the air contaminated (hereinafter, referred to as "contaminated air") passes is referred to as a negative pressure contaminated plenum 111.

The negative pressure contaminated plenum 111 is a contaminated region that bacteria and viruses 122 handled in the work space 104 may reach. The air suctioned into the blower 110 is pressurized in a pressure chamber 112, and a part of the pressurized air is filtered by an air supply HEPA filter 113, which is an air cleaner, to be supplied into the work space 104 as clean air. The other part of the air suctioned into the blower 110 is filtered by an exhaust HEPA filter 114, which is an air cleaner, to be discharged outside the device as clean air.

A blowout air flow 115 supplied into the work space 104 cleans the inside of the work space 104, and a part and the other part of the blowout air flow 115 are suctioned from a front suction slit 116 and a back air suction port 117 to be suctioned into the blower 110 through the circulation flow path 109.

As the performance of the safety cabinet 100, it is very important that the worker is not infected with the bacteria and viruses 122 handled thereinside, and an air barrier isolates the air in the work space 104 from the air outside the safety cabinet 100 to obtain the function.

Here, the air barrier is an atmosphere wall that is formed by the flow of the air blown out to the work space 104 since a majority of the air 107 flowing in from the front opening 102 and the blowout air flow 115 delivered to the work space 104 are suctioned from the front suction slit 116, and prevents the flow of the air 107 from the front opening 102 into the work space 104.

A work chamber see-through window 119 through which the work space 104 can be seen is provided on one side surface side of the work space 104. Furthermore, a steel plate member separates the circulation flow path 109, and the work chamber see-through window 119 isolates the inside and the outside of the work chamber from each other. The work chamber see-through window 119 is made of a transparent material such as tempered glass or laminated glass.

An imaging device 121 such as a network camera is installed outside the work chamber see-through window 119. The imaging device 121 usually requires a power supply wiring or a LAN wiring.

A connection opening 120 that connects the safety cabinet 100 to another device is provided on the other side surface side facing one side surface on which the imaging device 121 is disposed. For example, an automatic cell culture device and the safety cabinet 100 are connected via the connection opening 120. In that case, after cells are cultured in the automatic cell culture device, the cultured cells in a petri dish are transferred to the safety cabinet 100 via the connection opening 120, and can be observed in the work space 104 of the safety cabinet 100, the work space 104 being clean.

In addition, since the cells are transferred to a new medium in the automatic cell culture device or the safety cabinet 100 via the connection opening 120, and subculture work can be performed, the risk of contamination can be suppressed.

If a transfer error occurs when cells are transferred from the automatic cell culture device to the safety cabinet 100 by a robot, the worker is notified of the transfer error by an alarm buzzer or the like, but the state of a transfer unit is required to be recorded by the imaging device 121. Since the imaging device 121 is disposed above the position of the connection opening 120, the imaging device 121 can reliably record the inside of the connection opening 120. In addition, since the imaging device 121 is disposed in front of the center in a depth direction of the safety cabinet 100, the imaging device 121 can reliably record a work region.

As described above, since the imaging device 121 is disposed outside the one side surface of the work space 104, the one side surface facing the connection opening 120, not only the work space 104 and the work bench 108 but also the inside of the connection opening 120 can be monitored. For this reason, the imaging device 121 can record all regions where cells are manipulated in the safety cabinet 100.

Since the imaging device 121 is disposed in a general chamber other than a contaminated space such as the work space 104 or the negative pressure contaminated plenum 111, the entirety of the imaging device 121 is not in contact with contaminated air. Accordingly, wiping (disinfection) or sterilization before and after work or during changeover (when a sample to be handled is changed) is not required. In addition, since the imaging device 121 does not become resistance to the flow path due to being not disposed in the work space 104, a stable air flow is formed in the work space 104, so that the power consumption of the blower or the like can be suppressed.

In addition, even when the entirety of the work space 104 is sterilized with formaldehyde gas or the like in order to detoxify contaminants, since the imaging device 121 is not disposed in the work space 104, the imaging device 121 does not require sterilization, and a failure in the imaging device 121 can be prevented.

In addition, the irradiation of UV-C waves that are ultraviolet rays of the sterilization lamp 106 promotes deterioration of a resin or the like, but the transmissivity of glass for the UV-C waves is substantially 0%. For this reason, when a glass material is used as the material of the work chamber see-through window 119, the use of the sterilization lamp 106 can be prevented from causing deterioration of the imaging device 121 such as a network camera. In addition, since the sterilization lamp 106 is disposed in the upper portion of the back surface of the work space 104, and the sterilization lamp 106 is separated from the imaging device 121, deterioration of the imaging device 121 can be prevented.

Furthermore, since the safety cabinet 100 is assembled with steel plate components, when a network camera is used as the imaging device 121 in the work space 104 and data is accumulated by a wireless LAN, the steel plate components may act as obstacles to become barriers to wireless communication.

In the case of the safety cabinet 100 of the first embodiment, since the imaging device 121 is disposed outside a steel plate, which surround the work space, to not become barriers, data can be accumulated by the wireless LAN. In addition, there are merits such as being able to omit wiring work, saving wirings, obtaining a neat appearance, and being able to prevent dust from being accumulated in a wiring portion.

Figure 4:
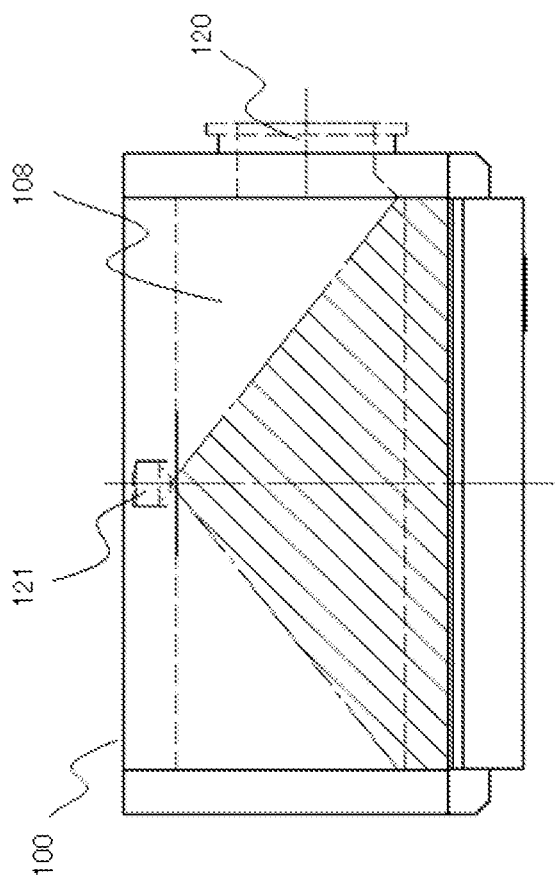
FIG. 4 is an internal structural view of a safety cabinet of a comparative example as seen from the top.

FIG. 4 is an internal structural view of the safety cabinet 100 of a comparative example as seen from the top.

Figure 5:
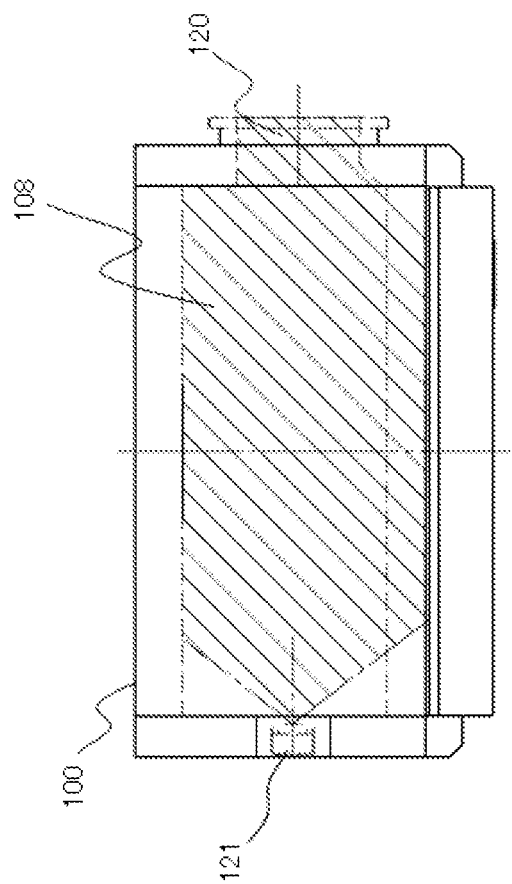
FIG. 5 is an internal structural view of the safety cabinet in the first embodiment as seen from the top.

FIG. 5 is a view illustrating the internal structure of the safety cabinet 100 in the first embodiment as seen from the top.

Diagonally-lined regions in FIGS. 4 and 5 illustrate the angles of view of the imaging device 121, and represent regions where an image can be captured.

In the safety cabinet 100 of the comparative example, as illustrated by the diagonally-lined region of FIG. 4, the region where an image can be captured is mainly the vicinity of the center of the work bench 108.

In the first embodiment, as illustrated by the diagonally-lined region of FIG. 5, an image of the entire region on the work bench 108 can be captured, and an image of the entire region inside the connection opening 120 can be captured. In addition, an image of the entire area on the work bench 108 can be captured even in the safety cabinet 100 which has a structure where the width of the work bench 108 is wide in consideration of two-person work and the like. Since the corners of the work bench are not work regions, images of the corners are usually not to be captured; however, when images of the corners are required to be captured, the position of the imaging device 121 can be set at a distance from the work bench 108 to allow images of all the corners to be captured.

Figure 6:
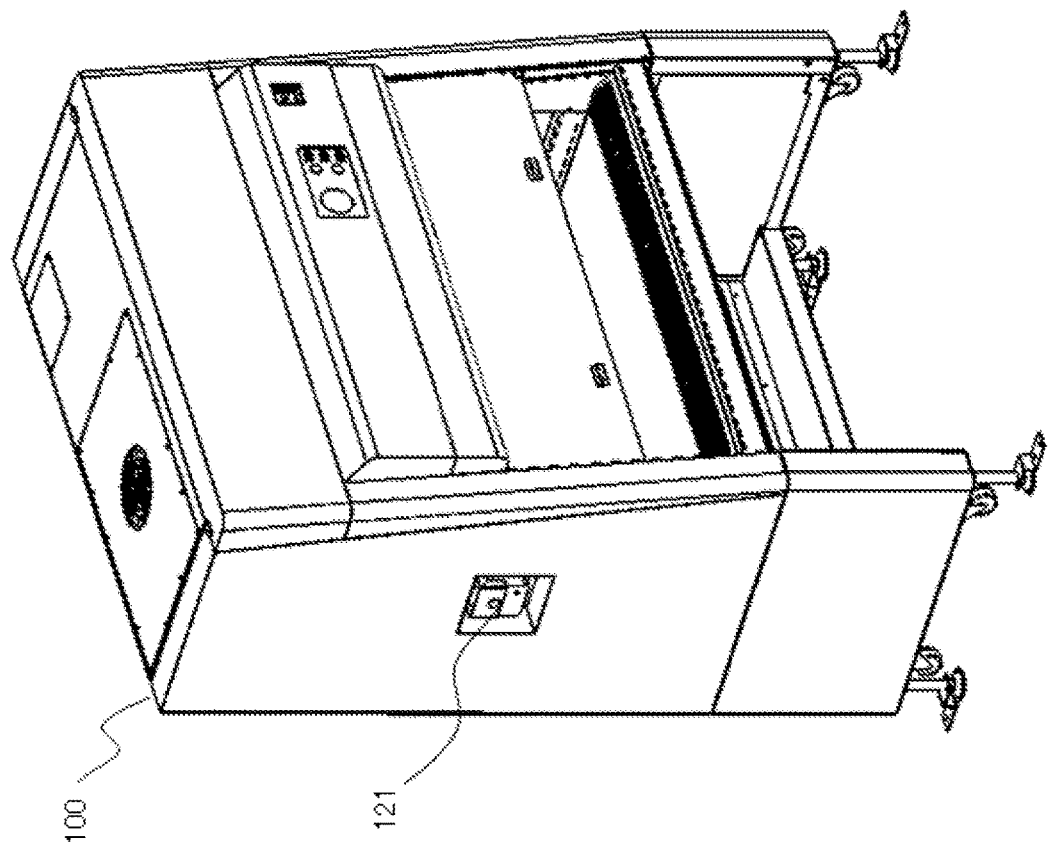
FIG. 6 is a perspective view of the safety cabinet in the first embodiment.

FIG. 6 is an example of a perspective view of the safety cabinet 100 in the first embodiment. Since the imaging device 121 is disposed on the outside which is isolated from the work space 104 of the safety cabinet 100 by the work chamber see-through window 119, even when the bacteria and viruses 122 are handled in the work space 104, there is no risk of contamination of the imaging device.

In addition, the imaging device 121 is disposed in a recessed portion that does not protrude from the safety cabinet 100. When a cover is put on the recessed portion in which the imaging device 121 is disposed, an outer surface of the safety cabinet 100 has a flat structure, the ease of cleaning is improved.

According to the present embodiment, an image of the entirety of the work space can be captured by the imaging device such as a network camera. In addition, the air flows are not disturbed, diffused reflection by the illumination lamp is suppressed, and a work process in the safety cabinet can be recorded as a good still image or video. Then, in the present embodiment, since the imaging device is installed in a region other than the contaminated regions, wiping (disinfection) or sterilization before and after work or during changeover (when a sample to be handled is changed) is not required.

Second Embodiment

Figure 7:
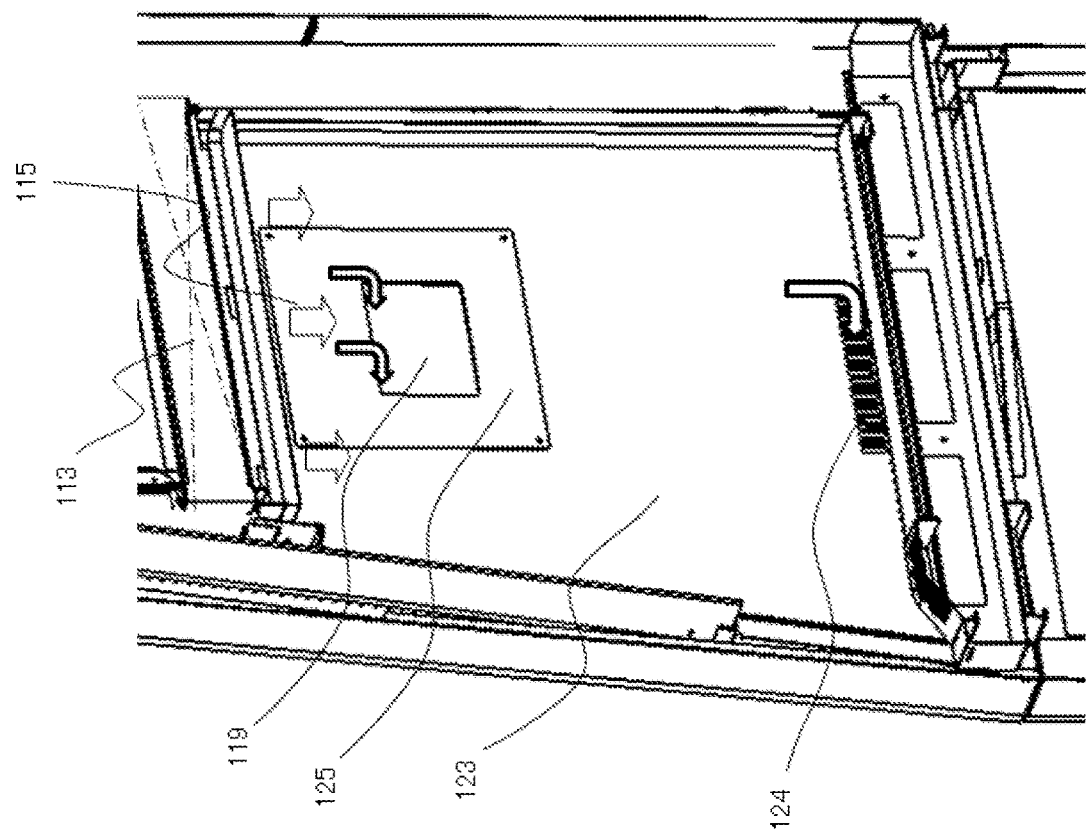
FIG. 7 is a structural view of a left side portion of a safety cabinet in a second embodiment.

FIG. 7 is a structural view of a left side portion of the work space 104 of the safety cabinet 100 in a second embodiment as seen from inside the work space (work chamber). The speed of the blowout air flow 115, which is clean air that has passed through the air supply HEPA filter 113, is increased along a wall surface of a left side lining 123. A part of the blowout air flow 115 is drawn into a very small gap of approximately 1 to 3 mm between the work chamber see-through window 119 and a square hole of a work chamber see-through window cover 125, to flow to the circulation flow path 109 and then to circulate inside the safety cabinet 100. In addition, a part of the blowout air flow 115 is drawn into a left side slit 124 to circulate inside the safety cabinet 100.

Figure 8:
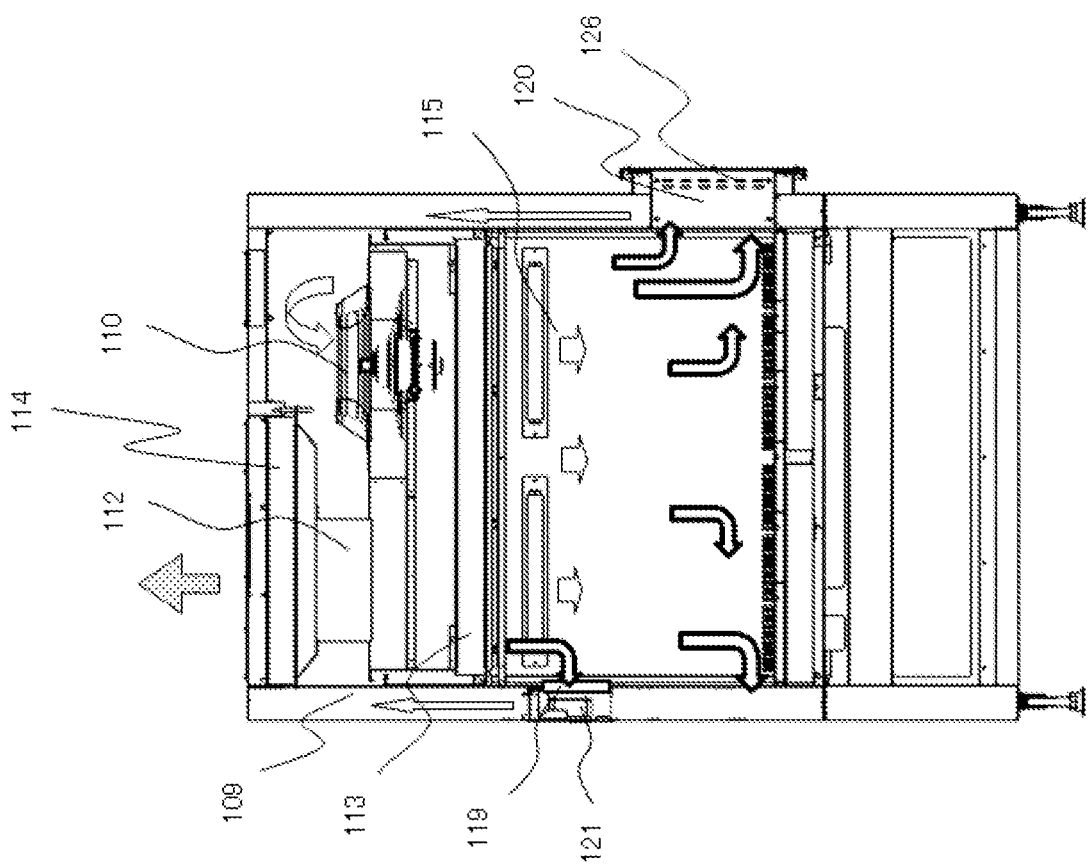
FIG. 8 is a view of an example illustrating air flows in a work space of the safety cabinet in the second embodiment.

FIG. 8 is a view illustrating air flows in the work space 104 of the second embodiment. The blowout air flow 115 is also drawn into a connection opening slit 126 of the connection opening 120, which is opened with respect to the circulation path illustrated in FIG. 7 to prevent mutual contamination between the safety cabinet 100 and a device connected thereto. For this reason, air flows balanced rightward and leftward are formed in the work space 104. The air flows that satisfy a test of preventing mutual contamination between samples in the safety cabinet 100 for biohazard countermeasure conforming to or according to JIS K3800 can be secured, so that mutual contamination in the work space 104 can be prevented.

REFERENCE SIGNS LIST

100 Safety cabinet
101 Worker
102 Front opening
103 Front shutter
104 Work space
105 Illumination lamp
106 Sterilization lamp
107 Air in general chamber
108 Work bench
109 Circulation flow path
110 Blower
111 Negative pressure contaminated plenum
112 Pressure chamber
113 Air supply HEPA filter
114 Exhaust HEPA filter
115 Blowout air flow
116 Front suction slit
117 Back air suction port
119 Work chamber see-through window
120 Connection opening
121 Imaging device
122 Bacteria and viruses
123 Left side lining
124 Left side slit
125 Work chamber see-through window cover
126 Connection opening slit

The invention claimed is:

1. A safety cabinet comprising:
a work space where work is performed;
a front panel disposed in a front surface of the work space; and
an air cleaner that cleans air to be supplied to the work space,
wherein an imager is disposed on a first side surface of the work space, and a connection opening is disposed on a second side surface of the work space,
wherein a work chamber see-through window is disposed between the work space and the imaging device, and
wherein an air flow that has passed through the air cleaner flows to a circulation path from a gap between the work chamber see-through window and a work chamber see-through window cover.

2. The safety cabinet according to claim 1, wherein the imager is disposed above a position of the connection opening.

3. The safety cabinet according to claim 1,
wherein the imager is disposed at a position to not protrude from a device main body.

4. The safety cabinet according to claim 1,
wherein a sterilization lamp is disposed in an upper portion of a back surface of the work space.

5. The safety cabinet according to claim 1,
wherein the imager is disposed outside a steel plate surrounding the work space.

* * * * *